US009962120B2

(12) United States Patent
Aoyama

(10) Patent No.: US 9,962,120 B2
(45) Date of Patent: May 8, 2018

(54) SLEEP STATE MANAGEMENT DEVICE, SLEEP STATE MANAGEMENT METHOD, AND SLEEP STATE MANAGEMENT PROGRAM

(71) Applicant: OMRON HEALTHCARE Co., Ltd., Kyoto (JP)

(72) Inventor: Hiroaki Aoyama, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 67 days.

(21) Appl. No.: 14/388,039

(22) PCT Filed: Nov. 12, 2012

(86) PCT No.: PCT/JP2012/079285
§ 371 (c)(1),
(2) Date: Sep. 25, 2014

(87) PCT Pub. No.: WO2013/145416
PCT Pub. Date: Oct. 3, 2013

(65) Prior Publication Data
US 2015/0038882 A1    Feb. 5, 2015

(30) Foreign Application Priority Data

Mar. 26, 2012  (JP) ................................. 2012-069609

(51) Int. Cl.
*A61B 5/00* (2006.01)
*A61B 5/11* (2006.01)
*G01H 17/00* (2006.01)

(52) U.S. Cl.
CPC ............... *A61B 5/486* (2013.01); *A61B 5/11* (2013.01); *A61B 5/1123* (2013.01);
(Continued)

(58) Field of Classification Search
CPC ... A61B 5/1102; A61B 5/1116; A61B 5/1118; A61B 5/1123; A61B 5/6887;
(Continued)

(56) References Cited

U.S. PATENT DOCUMENTS 5,724,990 A * 3/1998 Ogino .................. A61B 5/6887
600/587
9,433,377 B2 * 9/2016 Aoyama ............... A61B 5/4812
(Continued)

FOREIGN PATENT DOCUMENTS

JP    2007-61503 A     3/2007
JP    2007-252747 A   10/2007
(Continued)

OTHER PUBLICATIONS

ProQuest Machine Translation of JP 2010-094216.*
(Continued)

*Primary Examiner* — David J McCrosky
(74) *Attorney, Agent, or Firm* — Osha Liang LLP

(57) ABSTRACT

A control unit makes a provisional determination as to whether or not a measurement subject is moving using a detection signal from a sensor that detects movement in bedding on which the measurement subject is sleeping. In the case where at least one of a first period, in which periods determined to have body movement repeat cyclically, and a second period, in which a period determined to have body movement continues for at least a predetermined amount of time, has occurred, at least one of a period in the first period determined to have body movement and the second period are corrected to a period of no body movement.

7 Claims, 8 Drawing Sheets

(52) U.S. Cl.
CPC .......... *A61B 5/4806* (2013.01); *A61B 5/4809* (2013.01); *A61B 5/4815* (2013.01); *A61B 5/6892* (2013.01); *A61B 5/7278* (2013.01); *A61B 5/7282* (2013.01); *G01H 17/00* (2013.01)

(58) Field of Classification Search
CPC ... A61B 5/6891; A61B 5/6892; A61B 5/4806; A61B 5/4809; A61B 5/4812; A61B 5/4815; A61B 5/4818; A61B 5/7239; A61B 5/7242; A61B 5/7203; A61B 5/7207; A61B 5/721; A61B 5/7214; A61B 5/7217; A61B 5/7221; G01H 17/00
USPC .......................................... 600/300, 587, 595
See application file for complete search history.

(56) References Cited

U.S. PATENT DOCUMENTS

2004/0034285 A1* 2/2004 Sahashi .................. 600/300
2007/0106183 A1* 5/2007 Suzuki et al. ............ 600/595
2012/0253142 A1* 10/2012 Meger ................ A61B 5/7221
600/301

FOREIGN PATENT DOCUMENTS

| JP | 2007-292514 A | | 11/2007 |
|---|---|---|---|
| JP | 2008-125595 A | | 6/2008 |
| JP | 2010-94216 A | | 4/2010 |
| JP | 2010094216 A | * | 4/2010 |
| JP | 2010-273831 A | | 12/2010 |

OTHER PUBLICATIONS

Binary. (1992). In C. G. Morris (Ed.), Academic Press Dictionary of Science and Technology (4th ed.). Oxford, UK: Elsevier Science & Technology. Retrieved from <http://search.credoreference.com/content/entry/apdst/binary/0?institutionId=743> on Sep. 14, 2017.*
International Search Report for corresponding International Application No. PCT/JP2012/079285, dated Dec. 18, 2012 (1 page).
Written Opinion for corresponding International Application No. PCT/JP2012/079285, dated Dec. 18, 2012 (6 page).

* cited by examiner

SLEEP STATE MANAGEMENT DEVICE, SLEEP STATE MANAGEMENT METHOD, AND SLEEP STATE MANAGEMENT PROGRAM

TECHNICAL FIELD

The present invention relates to sleep state management devices, sleep state management methods, and sleep state management programs.

BACKGROUND ART

Ensuring the quality and appropriate state of sleep is essential for maintaining one's health. It is necessary to understand a sleep state, including an amount of sleep time from when a person goes to bed to when the person wakes, the depth of the sleep, and so on, in order to evaluate the sleep state. The devices disclosed in Patent Literature 1-3 have been proposed as devices for understanding such a sleep state.

Patent Literature 1 discloses a device that determines a subject is in bed when the subject's heart rate, measured based on a signal detected from a sensor, exceeds an in-bed determination threshold, and in the case where, in segments in which it has been determined that the subject is in bed, a degree of variation in the signal level in a plurality of stable segments (segments where the signal level does not vary greatly) is low, determines that a heart rate distribution in the segments for which the determination has been made is due to external noise rather than biological factors.

Patent Literature 2 and Patent Literature 3 disclose devices that determine a sleep state of a measurement subject using a vibration sensor that detects vibrations in a location where the measurement subject is sleeping.

CITATION LIST

Patent Literature

Patent Literature 1: JP 2010-94216A
Patent Literature 2: JP 2010-273831A
Patent Literature 3: JP 2007-61503A

SUMMARY OF INVENTION

Technical Problem

When using a sensor to detect vibrations in the bedding where the measurement subject is sleeping as disclosed in Patent Literature 2 and 3, the level of the signal outputted from the sensor is extremely low compared to that from a sensor that directly detects body movement, such as that disclosed in Patent Literature 1.

Accordingly, it becomes difficult to accurately determine whether body movements are occurring when there are external disturbances such as vibrations in the area where the bedding is placed (vibrations produced by automobiles traveling in the vicinity, earthquakes, and so on, for example), vibrations in the device produced by wind from a fan or the like, vibrations produced by the vibrator in a mobile phone placed on the bedding, and so on.

Recent years have seen an increase in demand for improving the quality of sleep, and as such there is demand for the development of a device that can accurately determine a sleep state without being susceptible to the aforementioned external disturbances.

Having been achieved in light of the aforementioned circumstances, it is an object of the present invention to provide a sleep state management device, a sleep state management method, and a sleep state management program capable of accurately determining whether or not a measurement subject's body is moving without being susceptible to external disturbances.

Solution to Problem

A sleep state management device according to the present invention manages a measurement subject's sleep state based on body movement in the measurement subject, and includes a sensor unit that detects movement in bedding where the measurement subject is sleeping and a body movement determination unit that determines whether or not there is body movement in the measurement subject using a detection signal from the sensor unit; in the case where at least one of a first period, in which a period without body movement in which it has been determined that there is no body movement using the detection signal or a period of body movement in which it has been determined that there is body movement using the detection signal occur cyclically, and a second period, in which the period of body movement continues for at least a predetermined amount of time, has occurred, the body movement determination unit corrects at least one of the period of body movement in the first period and the second period to a determination of a period without body movement.

A sleep state management method according to the present invention manages a measurement subject's sleep state based on body movement in the measurement subject, and includes a body movement determination step of determining body movement in the measurement subject using a detection signal from a sensor unit that detects movement in bedding where the measurement subject is sleeping; in the case where at least one of a first period, in which a period without body movement in which it has been determined that there is no body movement using the detection signal or a period of body movement in which it has been determined that there is body movement using the detection signal occur cyclically, and a second period, in which the period of body movement continues for at least a predetermined amount of time, has occurred, the body movement determination step corrects at least one of the period of body movement in the first period and the second period to a determination of a period without body movement.

A sleep state management program according to the present invention is a program for causing a computer to execute the steps of the aforementioned sleep state management method.

Advantageous Effects of Invention

According to the present invention, a sleep state management device, a sleep state management method, and a sleep state management program capable of accurately determining whether or not a measurement subject's body is moving without being susceptible to external disturbances can be provided.

DESCRIPTION OF EMBODIMENTS

Hereinafter, an embodiment of the present invention will be described with reference to the drawings.

Figure 1:
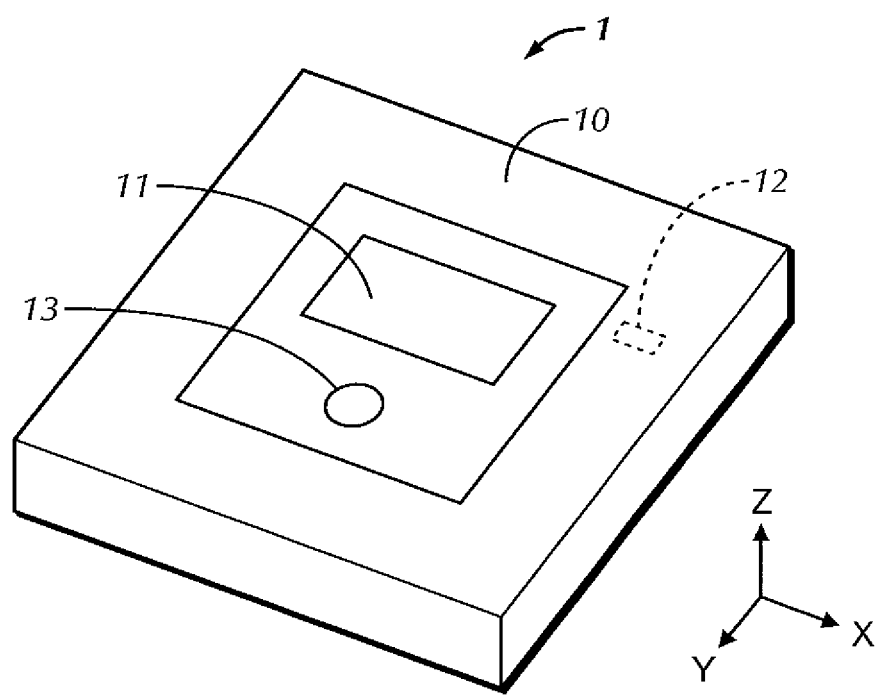
FIG. 1 is an external view illustrating the configuration of a sleep state management device 1 embodying the present invention.

FIG. 1 is an external view illustrating the configuration of a sleep state management device 1 embodying the present invention.

The sleep state management device 1 includes a display unit 11, an operating unit 13, and a sensor 12, which are provided in a box-shaped housing 10.

The display unit 11 and the operating unit 13 are provided in an upper surface (one of two surfaces parallel to an XY plane) of the housing 10. The sensor 12 is provided within the housing 10.

The sleep state management device 1 is used by being placed on a measurement subject's bedding, such as a bed or a futon, with a base surface (the other of the two surfaces parallel to the XY plane) of the housing 10 making contact with the bedding.

The display unit 11 displays various types of menus and the like of the sleep state management device 1, and is configured of a liquid-crystal display device, for example.

The operating unit 13 is an interface for powering the sleep state management device 1 on, making various types of operations, and so on, and is configured of a button or the like, for example.

The sensor 12 is a three-axis accelerometer, and detects an acceleration in an X-axis direction, an acceleration in a Y-axis direction, and an acceleration in a Z-axis direction.

A detection signal resulting from detection performed by the sensor 12 when the sleep state management device 1 is placed on the bedding corresponds to movement (vibration) in the bedding. In other words, the sensor 12 functions as a vibration detection sensor that detects movement in the bedding that the measurement subject is sleeping on.

In this manner, the sensor 12 detects movement in the bedding produced when the measurement subject moves. Movement in the bedding produced when the measurement subject's body moves is slighter than the measurement subject's body movement itself. Accordingly, the level of the detection signal resulting from detection performed by the sensor 12 is extremely low.

Figure 2:
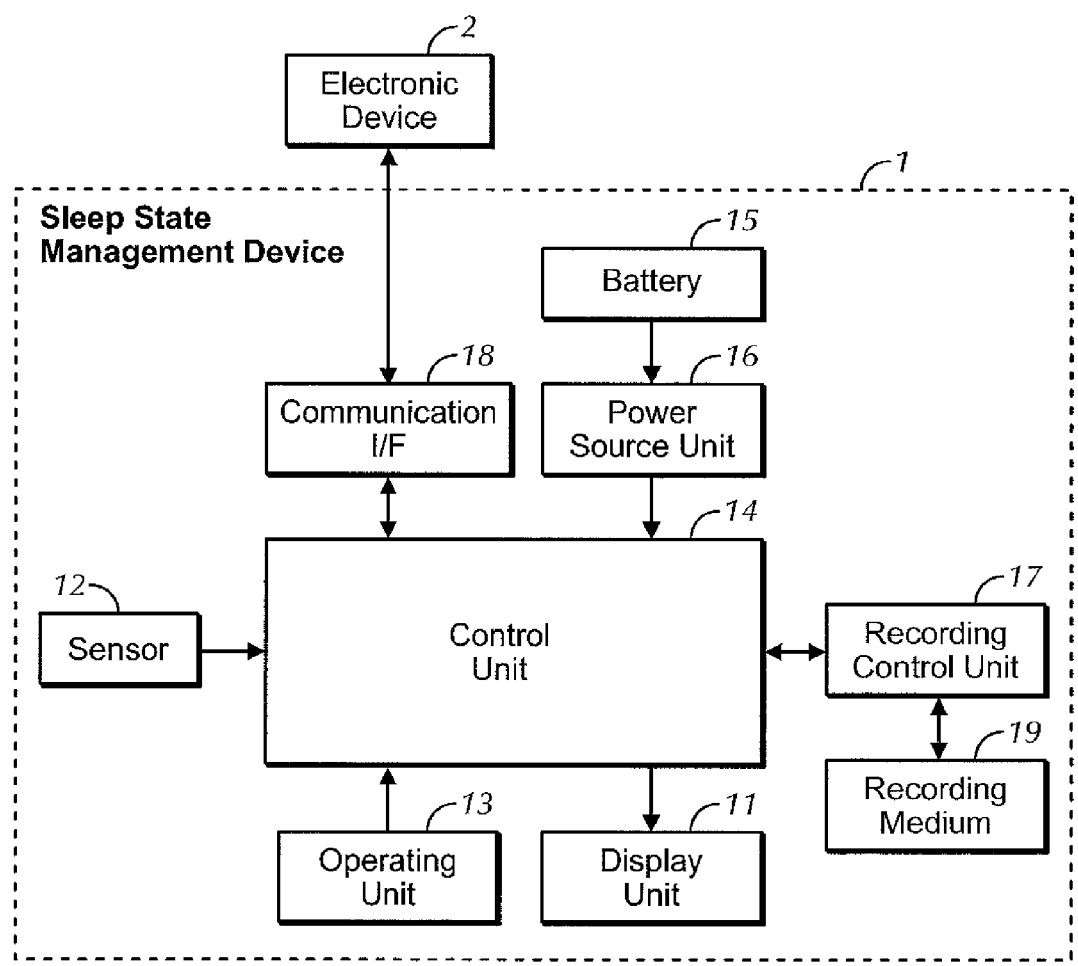
FIG. 2 is a block diagram illustrating the internal configuration of the sleep state management device 1 shown in FIG. 1.

FIG. 2 is a block diagram illustrating the internal configuration of the sleep state management device 1 shown in FIG. 1.

In addition to the display unit 11, the sensor 12, and the operating unit 13 shown in FIG. 1, the sleep state management device 1 includes a battery 15, a power source unit 16, a recording control unit 17, a communication interface (I/F) 18, a recording medium 19, and a control unit 14 that performs various types of computational processes and controls the sleep state management device 1 as a whole.

The battery 15 is a button battery, for example. The power source unit 16 supplies power from the battery 15 to the various units in the sleep state management device 1 via the control unit 14.

The recording medium 19 records data generated by the control unit 14, and is configured of a flash memory or the like, for example.

The recording control unit 17 is a driver for the recording medium 19, and writes data into the recording medium 19 and reads data out from the recording medium 19 in response to instructions from the control unit 14.

The communication I/F 18 is an interface for the sleep state management device 1 to communicate, wirelessly or over wires, with an external electronic device 2 (a personal computer, a mobile phone such as a smartphone, or the like).

The detection signal from the sensor 12 is converted into a digital signal and inputted into the control unit 14. The control unit 14 is configured primarily of a CPU (a central processing unit), carries out various types of computational processes based on the inputted detection signal, and records data based on the results of the computational processes into the recording medium 19.

The operating unit 13 is connected to the control unit 14; a signal resulting from the operating unit 13 being operated is inputted into the control unit 14, and the control unit 14 carries out control based on that signal. The control unit 14 also includes a ROM that stores programs executed by the CPU, a RAM serving as a work memory, and so on.

Operations of the sleep state management device 1 will be described next.

The measurement subject places the sleep state management device 1 on the bedding and makes an instruction to start recording the sleep state by operating the operating unit 13.

When the instruction to start recording has been made, the control unit 14 stores the detection signal resulting from detection performed by the sensor 12 (a digital value) in the RAM of the control unit 14. Note that in the case where an instruction to stop recording the sleep state has been made by the operating unit 13 being operated, the storage of the detection signal in the RAM is stopped.

Figure 3:
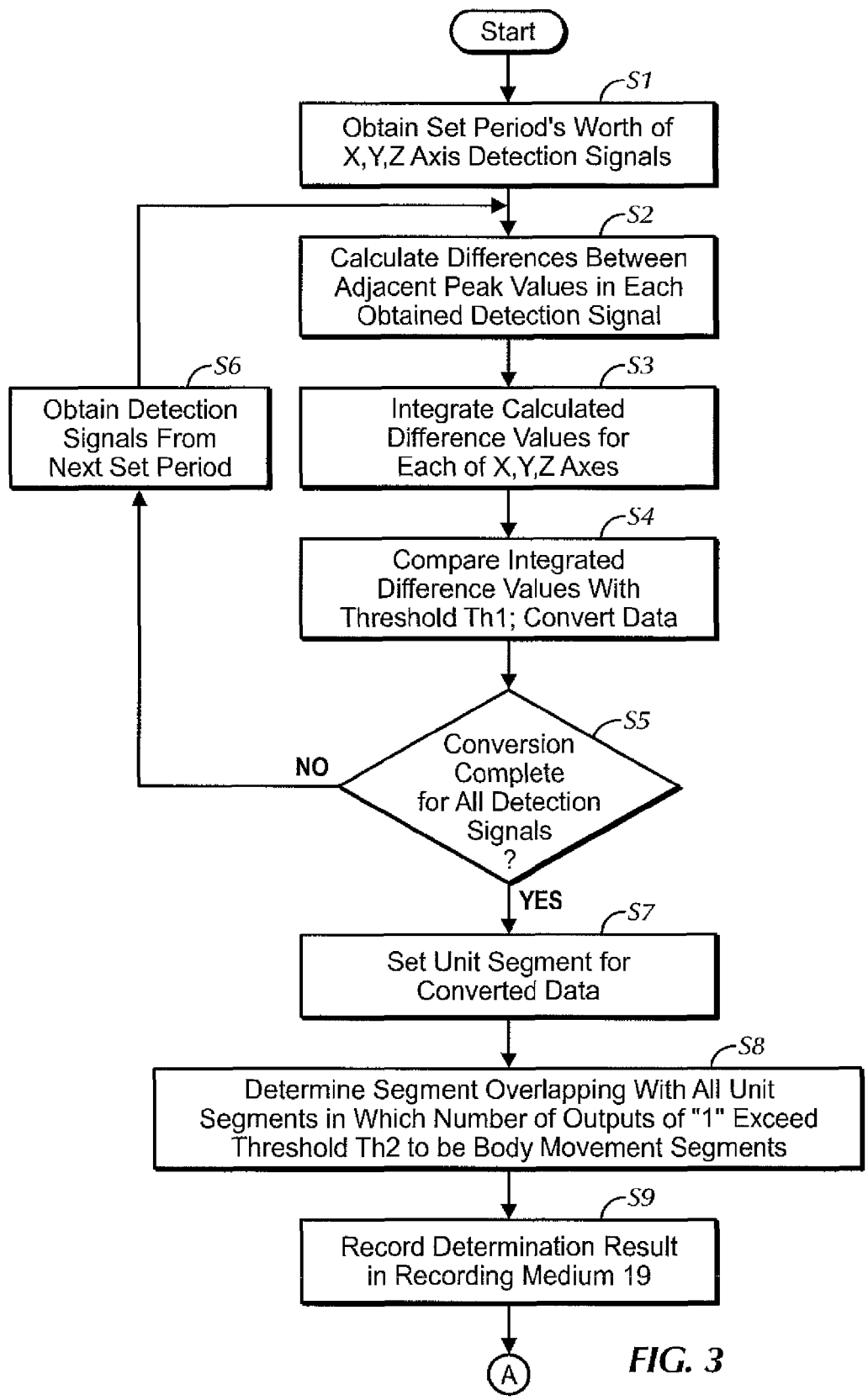
FIG. 3 is a flowchart illustrating operations performed by the sleep state management device 1 shown in FIG. 1.
Figure 4:
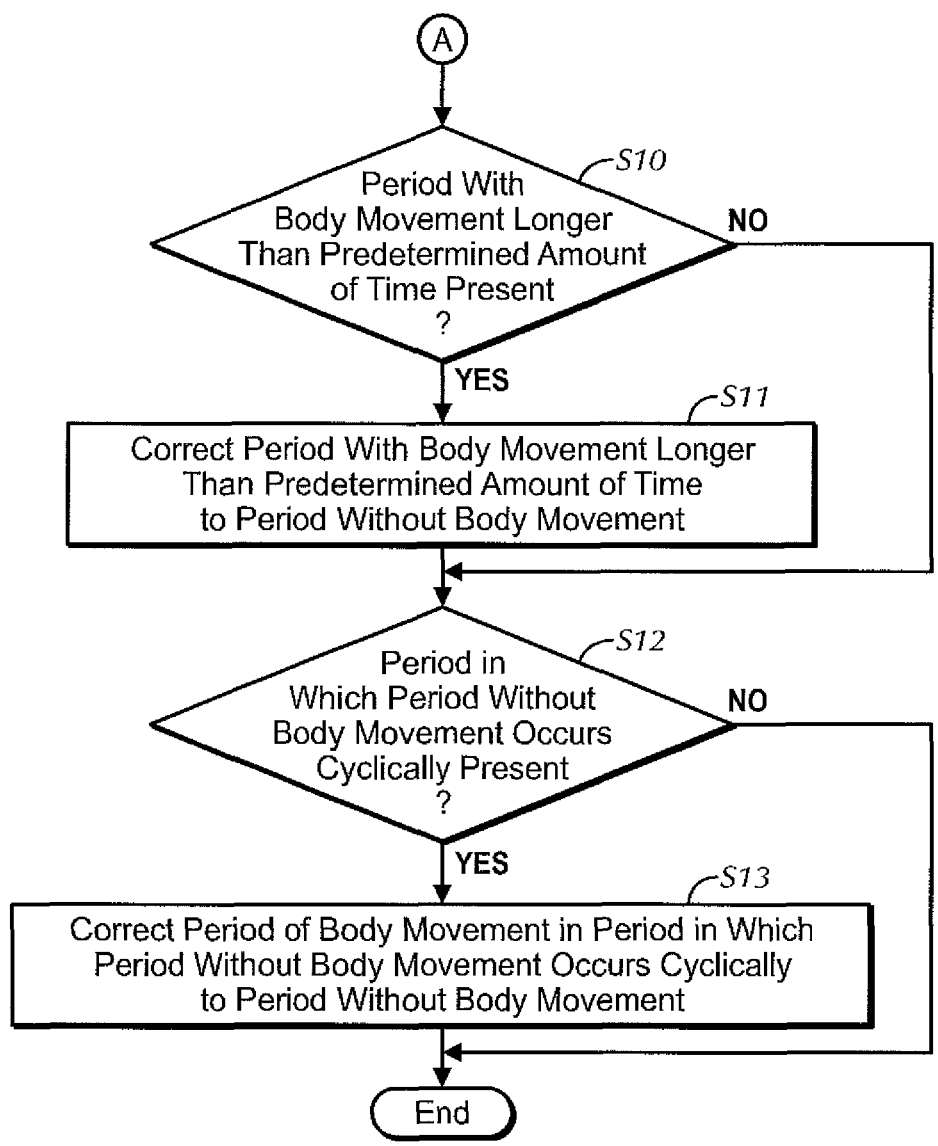
FIG. 4 is a flowchart illustrating operations performed by the sleep state management device 1 shown in FIG. 1.

FIGS. 3 and 4 are flowcharts illustrating operations in a process for determining body movement performed by the sleep state management device 1 shown in FIG. 1. The respective steps shown in FIGS. 3 and 4 are carried out by the CPU in the control unit 14 based on programs stored in the ROM. Meanwhile, the process for storing the detection signal is also carried out based on a program stored in the ROM.

When a length of the detection signal that enables peak values in the detection signal (mentioned later) to be detected has been stored in the RAM, the control unit 14 obtains, from the detection signal stored in the RAM, a set period's worth (here, 14 seconds, for example) of the detection signal (an X-axis detection signal, a Y-axis detection signal, and a Z-axis detection signal) (step S1).

Next, the control unit 14 calculates, from the obtained detection signals in the respective axes, differences between adjacent peak values (absolute values that disregard the positive/negative sign) (step S2).

Figure 5:
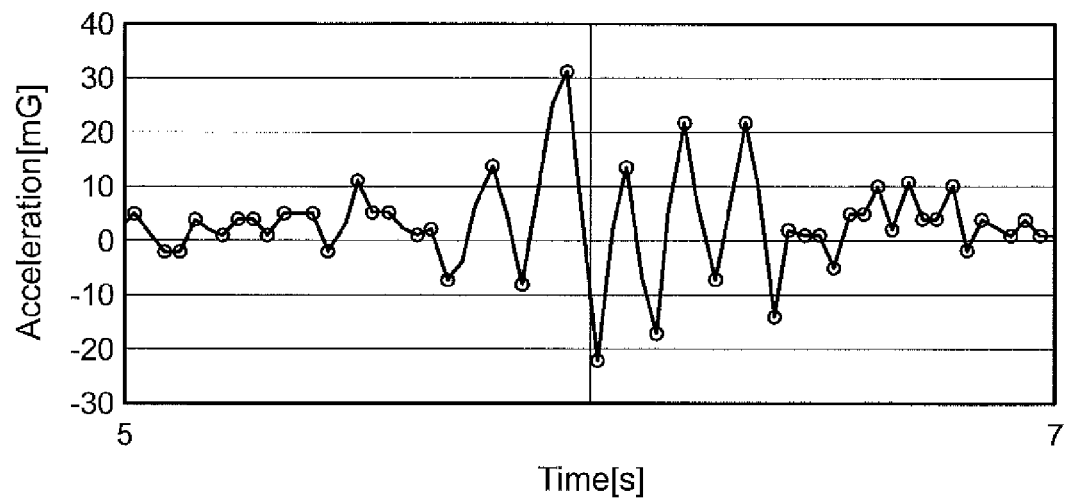
FIG. 5 is a diagram illustrating details of the process performed in step S2 of the flowchart shown in FIG. 3.

FIG. 5 is a diagram illustrating details of the process performed in step S2 of the flowchart shown in FIG. 3. FIG. 5 illustrates a waveform of the obtained (X-axis) detection signal, from seconds number 5 to 7 in the aforementioned set period (of 14 seconds).

In the aforementioned step S2, the control unit 14 first extracts the peak values from the waveform of the detection signal shown in FIG. 5.

The "peak values" are the values at points where the detected acceleration value switches from a high value to a lower value, levels out from a high value, switches from a low value to a higher value, and levels out from a low value (the points encircled in FIG. 5).

After extracting the peak values, the control unit 14 calculates a difference between each peak value and the peak values adjacent to that peak value (the adjacent peak values obtained before and after the stated peak value when taken in time series).

The control unit 14 then stores the calculated difference values in association with a time represented by a predetermined small segment (a period approximately equal to an estimated amount of time between peak values) that contains the time at which the peak value was obtained (the stated time being one of a start time, an end time, a midpoint time of the small segment, or the like).

The control unit 14 then integrates difference values in the X-axis detection signal, difference values in the Y-axis detection signal, and difference values in the Z-axis detection signal found in step S2 that correspond to the same time, and finds integrated values of the X-axis, Y-axis, and Z-axis difference values at each time (step S3).

Figure 6:
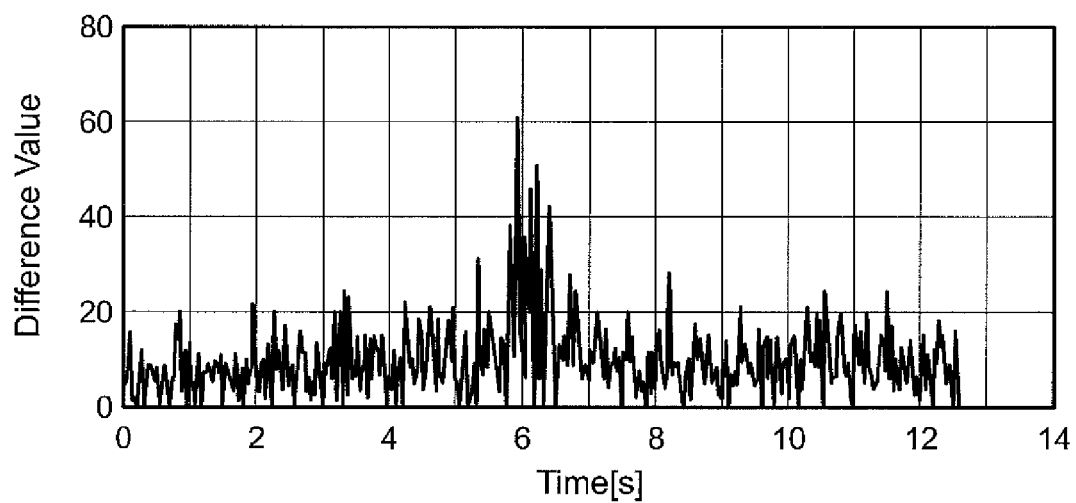
FIG. 6 is a diagram illustrating an example of integrated difference values obtained in step S3 of the flowchart shown in FIG. 3.

FIG. 6 is a diagram illustrating an example of integrated difference values obtained in step S3 of the flowchart shown in FIG. 3. FIG. 6 is a graph in which the integrated values of the difference values throughout the stated set period (14 seconds) have been plotted.

Figure 7:
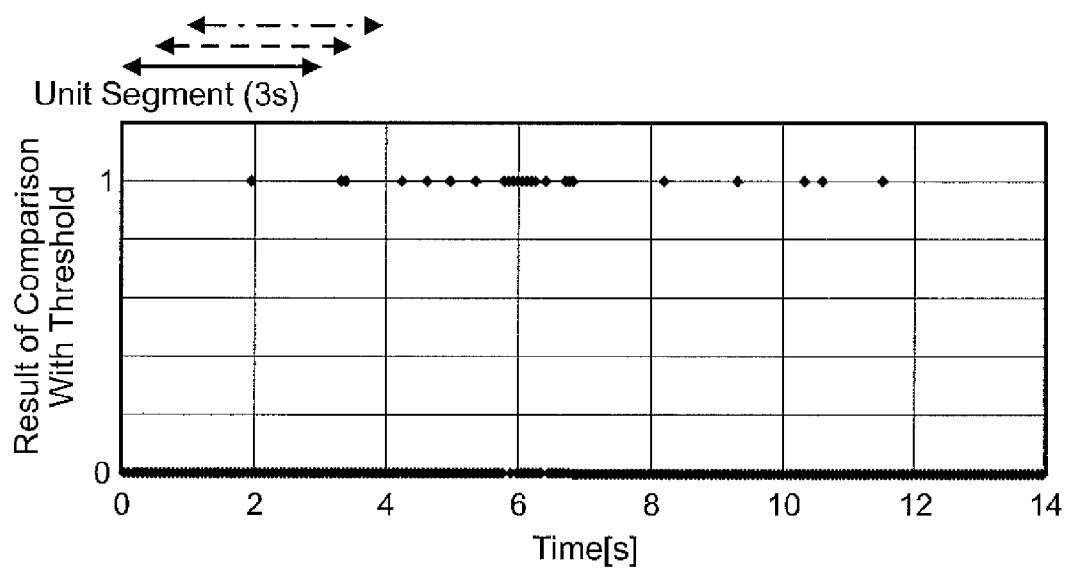
FIG. 7 is a diagram illustrating an example of data obtained in step S4 of the flowchart shown in FIG. 3.

Next, the control unit 14 compares the difference values found in step S3 with a threshold Th1, creates data, shown in FIG. 7, by converting data at times where the difference value exceeds the threshold to "1" and converting data at times where the difference value is less than or equal to the threshold to "0" (step S4), and stores the created data in the RAM.

FIG. 7 illustrates data obtained when the threshold Th1 is set to 20 for the data shown in FIG. 6.

For the difference values found in step S3, a greater value indicates a greater change in movement in the bedding where the measurement subject is sleeping.

The bedding moves not only due to the measurement subject moving, but also due to vibrations in the location where the bedding is placed. The sleep state management device 1 uses the sensor 12 to detect slight movements in the bedding.

As such, the detection signals from the sensor 12 also include signals resulting from fine vibrations in the location where the bedding is placed. The detection signals from the sensor 12 also contain noise unique to the sensor.

Such variations in the detection signal caused by fine vibrations in the location where the bedding is placed, noise unique to the sensor, and so on are extremely small compared to fluctuations in the detection signal caused by the measurement subject moving.

However, according to the sleep state management device 1, the influence of fine vibrations in the location where the bedding is placed, noise unique to the sensor, and so on is eliminated by comparing the difference values to the threshold Th1.

In other words, the sleep state management device 1 determines that the bedding is moving due to fine vibrations in the location where the bedding is placed, noise unique to the sensor, and so on at times when the data is less than or equal to the threshold Th1 of 20 in FIG. 6, and determines that it is likely that the bedding is moving due to the measurement subject moving at times where the data is greater than the threshold Th1 of 20 in FIG. 6.

As shown in FIG. 6, the stated difference values sometimes increase sporadically, and sometimes increase for a sustained period. It is known that a measurement subject's body movements occur for sustained periods, and thus sporadic increases in the difference values can be determined to be caused by factors aside from such body movements.

Accordingly, the control unit 14 determines whether or not the measurement subject is moving through step S8, which will be described later.

After step S4, the control unit 14 carries out the process of step S7 in the case where all of the detection signals stored in the RAM have undergone the processing of step S2 to step S4 (step S5: YES).

On the other hand, in the case where all of the detection signals stored in the RAM have not undergone the processing of step S2 to step S4 (step S5: NO), in step S6, the control unit 14 obtains the detection signals of the next set period (a period from seconds 14 to 28, for example) from the RAM and carries out the processing from step S2 on.

In step S7, the control unit 14 sets a unit segment (for example, a 3-second segment) for the converted data generated in step S4 every 0.5 seconds, for example.

That is, the control unit 14 sets the unit segments so as to be staggered by 0.5 seconds, resulting in a segment indicated by a solid line arrow in FIG. 7 (a segment from seconds 0 to 3), a segment indicated by a broken line arrow in FIG. 7 (a segment from seconds 0.5 to 3.5), a segment indicated by a dot-dash line arrow in FIG. 7 (a segment from seconds 1 to 4), and so on.

After step S7, the control unit 14 counts the number of pieces of data that are "1" in each unit segment that has been set, and determines that segments in which the number of pieces of data that are "1" is greater than a threshold Th2 are segments in which the measurement subject has moved, and that segments in which the number of pieces of data that are "1" is less than or equal to the threshold Th2 are segments in which the measurement subject has not moved.

Then, the control unit 14 determines that periods overlapping with all of the unit segments determined to contain body movement are periods of body movement, and that other periods are periods without body movement (step S8).

Next, the control unit 14 records the periods determined to contain body movement and the periods determined not to contain body movement in the recording medium 19 so as to be distinguishable from each other (step S9).

The data illustrated in FIG. 6 also changes due to movements in the bedding caused by factors aside from body movement (for example, vibrations from the vibrator of a mobile phone placed on the bedding, wind from a fan, or the like).

Figure 8:
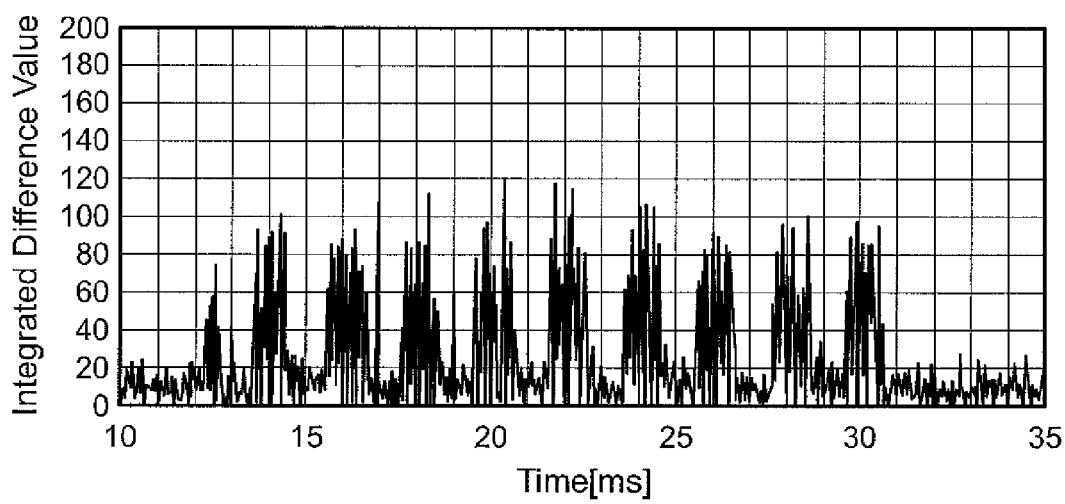
FIG. 8 is a diagram illustrating data obtained after the process of step S3 has been performed on a signal obtained as a result of detecting vibrations in bedding produced by the vibrator of a mobile phone.

FIG. 8 is a diagram illustrating a result of carrying out step S2 and step S3 of FIG. 3 on detection signals obtained in a period where the vibrator of a mobile phone is vibrating.

In the case where a difference value of, for example, 20 is set for the threshold Th1 in FIG. 8, it is determined, in step S8 of FIG. 3, that a period of body movement and a period without body movement are occurring cyclically.

Figure 9:
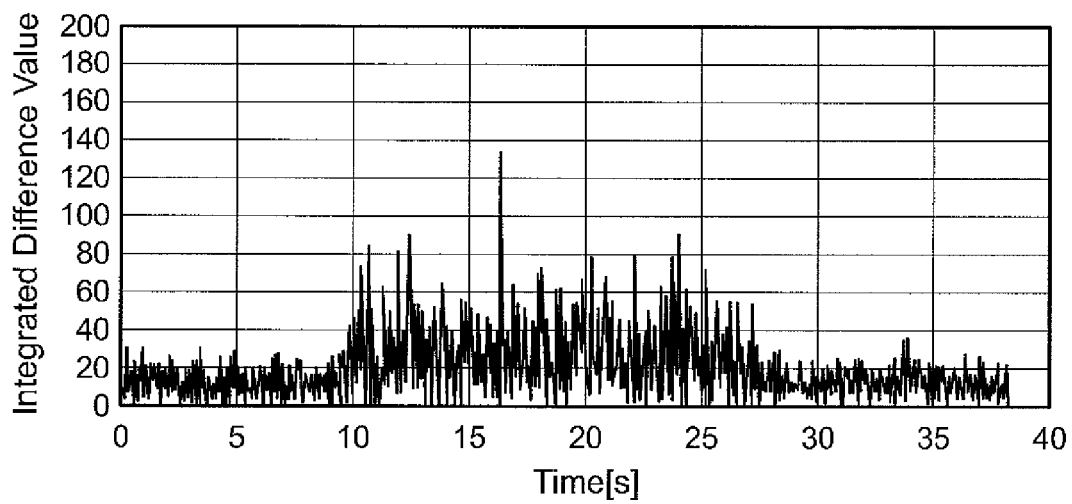
FIG. 9 is a diagram illustrating data obtained after the process of step S3 has been performed on a signal obtained as a result of detecting vibrations in a sensor itself produced by wind from a fan.

FIG. 9, meanwhile, is a diagram illustrating a result of carrying out step S2 and step S3 of FIG. 3 on detection signals obtained in a period where wind from a fan is striking the sleep state management device 1.

In the case where a difference value of, for example, 20 is set for the threshold Th1 in FIG. 9, it is determined, in step S8 of FIG. 3, that a period of body movement is occurring for a long length of time (more than 15 seconds, in the example shown in FIG. 9).

Thus there are cases where the determination result in step S8 of FIG. 3 is obtained from an erroneous determination in which a period that actually does not contain body movement is determined to be a period that does contain body movement.

Accordingly, after step S9, the sleep state management device 1 determines whether such an erroneous determination has been made, and in the case where such an erroneous determination has occurred, corrects the erroneous determination.

In step S10 of FIG. 4, the control unit 14 determines whether or not there is a period of body movement that is longer than a predetermined amount of time. The length of a period of body movement when body movement is actually occurring (that is, an average amount of time in which a person moves (turns over in bed)) is known experientially, and thus the stated predetermined amount of time is set to an amount of time that is longer than this length.

Figure 10:
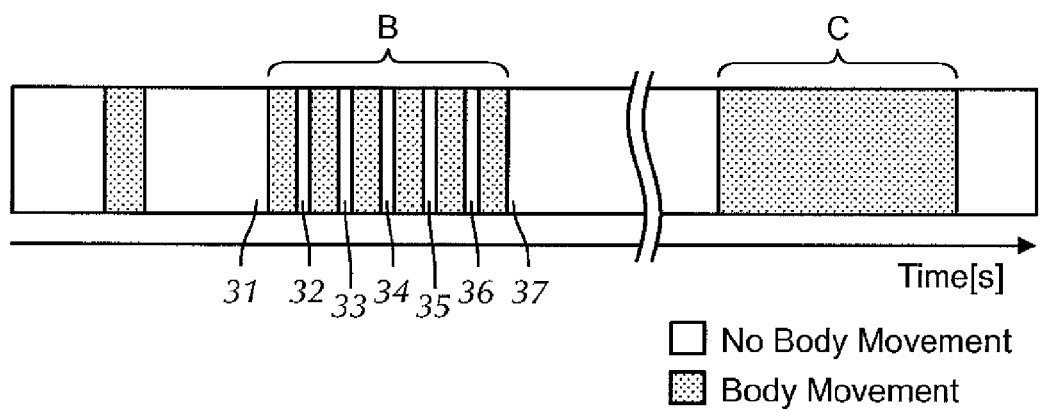
FIG. 10 is a diagram illustrating data recorded into a recording medium 19 in step S9 of the flowchart shown in FIG. 3.

FIG. 10 is a diagram illustrating data recorded into the recording medium 19 in step S9. In the data shown in FIG. 10, a period C corresponds to an area determined to be a period of body movement that is longer than the predetermined amount of time.

Figure 11:
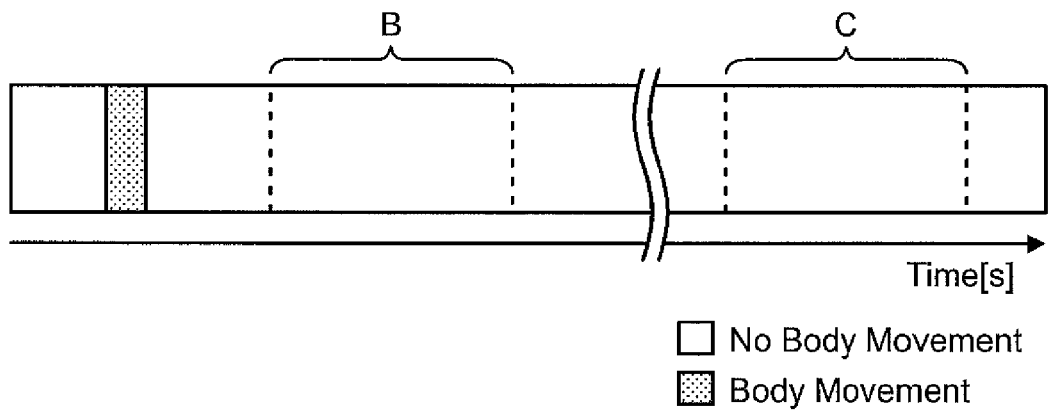
FIG. 11 is a diagram illustrating data obtained by correcting the data shown in FIG. 10.

When the result of the determination in step S10 is YES, the control unit 14 corrects the period of body movement that is longer than the stated predetermined amount of time in the data recorded in the recording medium 19 to a period without body movement, as indicated in FIG. 11 (step S11).

When the result of the determination in step S10 is NO, the control unit 14 determines whether or not there is a period in which a period without body movement is occurring cyclically (step S12).

Specifically, the control unit 14 determines a period in which three or more periods without body movement occur consecutively in an interval less than or equal to a predetermined amount of time to be a period in which a period without body movement is occurring cyclically. Assuming external disturbances that impart vibrations cyclically on the bedding in real day-to-day life, such as vibrations from a mobile phone, the predetermined amount of time can be determined experimentally from data, shown in FIG. 10, that has been measured when the stated assumed external disturbances are caused to actually occur.

In the data shown in FIG. 10, periods without body movement 31 to 37 occur consecutively on an interval that is less than the predetermined amount of time. In the case of such data, the control unit 14 determines that a period B, from the end of the period without body movement 31 to the start of the period without body movement 37, is a period in which a period without body movement is occurring cyclically.

When the result of the determination in step S12 is YES, the control unit 14 corrects the period of body movement in the period in which the period without body movement is occurring cyclically to a period without body movement, as indicated in FIG. 11 (step S13).

When the result of the determination in step S12 is NO after step S13, the control unit 14 records data into the recording medium 19 indicating that a period in which the frequency of body movement is greater than or equal to a predetermined value is a waking state period and a period in which the frequency of body movement is less than the predetermined value is a sleep state period, and then ends the body movement determination process.

Figure 12:
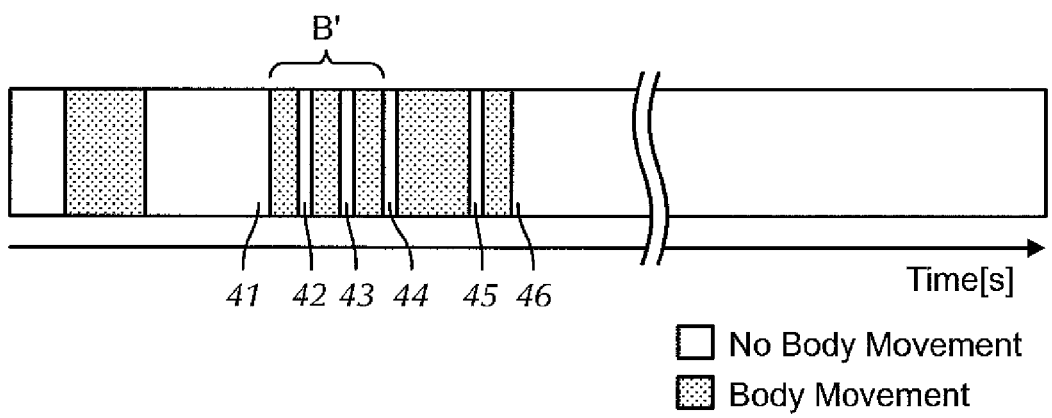
FIG. 12 is a diagram illustrating another example of data recorded into the recording medium 19 in step S9 of the flowchart shown in FIG. 3.

FIG. 12 illustrates data indicating an example of a body movement determination result in the case where there is body movement when a mobile phone vibrator is vibrating.

In the data shown in FIG. 12, an interval between a period without body movement 44 and a period without body movement 45 is greater than a predetermined amount of time. In the case of such data, the control unit 14 determines that a period B', from the end of the period without body movement 41 to the start of the period without body movement 44, is a period in which a period without body movement is occurring cyclically.

Figure 13:
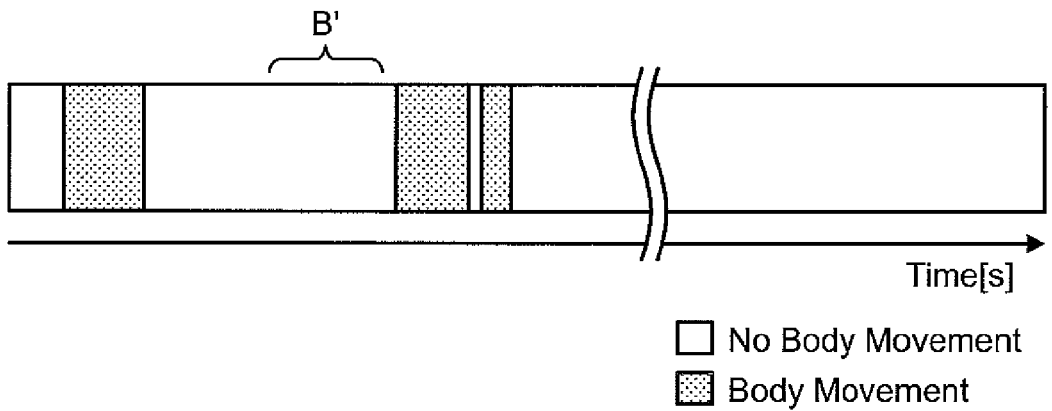
FIG. 13 is a diagram illustrating data obtained by correcting the data shown in FIG. 12.

The control unit 14 then corrects the period of body movement in the period B' to a period without body movement, as indicated in FIG. 13. In this manner, the cycle in which periods without body movement occur changes even in the case where there is body movement while a mobile phone vibrator is vibrating, thus eliminating erroneous determinations of body movement.

The data indicating the measurement subject's sleep state can be recorded into the recording medium 19 and the measurement subject's sleep state can be managed through the operations described thus far.

In this manner, the sleep state management device 1 calculates differences between adjacent peak values in the detection signal from the sensor 12 and determines whether or not there is body movement based on the difference values, and thus the sleep state management device 1 can detect even slight movement in the bedding and avoid missing such movement, improving the accuracy at which the body movement is determined.

In addition, in the case where a period has been determined to have body movement continues for greater than or equal to a predetermined amount of time, the sleep state management device 1 corrects that period to a period without body movement.

Accordingly, even in the case where wind from a fan, wind from the outside, or the like strikes the sleep state management device 1 and the sleep state management device 1 itself has shaken upon the bedding, that shaking is not erroneously determined to be from body movement, and the measurement subject's sleep state can be accurately managed as a result.

In addition, even if a period has been determined to have body movement, if that period takes place in a period in which periods without body movement occur cyclically, the sleep state management device 1 corrects the period of body movement to a period without body movement.

Accordingly, even in the case where a vibrator in a mobile phone placed upon the bedding has vibrated and the sleep state management device 1 itself shakes periodically, that shaking is not erroneously determined to be from body movement, and the measurement subject's sleep state can be accurately managed as a result.

Although the sleep state management device 1 determines a period in which periods without body movement occur cyclically to be a period of external disturbance, the sleep state management device 1 may also determine a period in which periods of body movement occur cyclically to be a period of external disturbance.

The period of body movement originally refers also to periods determined to have body movement due to noise, but the period without body movement is basically assumed to be a period in which there is no body movement. As such, determining a period in which periods without body movement occur cyclically to be a period of external disturbance makes it possible to increase the accuracy at which periods of external disturbance are determined.

Furthermore, according to the sleep state management device 1, a three-axis accelerometer is used as the sensor 12, and after the difference values found for the three axes are integrated in step S3 of FIG. 3, whether or not there is body movement is determined based on the integrated difference values; therefore, the determination as to whether or not there is body movement can be carried out having emphasized the difference values, which makes it possible to improve the accuracy of the determination.

Although the foregoing describes an example in which erroneous determinations due to mobile phone vibrators and erroneous determinations due to wind are corrected, an erroneous determination due to an earthquake, for example, can also occur.

When an earthquake occurs, periods of body movement occur consecutively for greater than or equal to a predetermined amount of time, in the same manner as with wind. Accordingly, an erroneous determination caused by an earthquake can also be corrected through the processes of step S10 and step S11.

Note that any sensor capable of detecting movement in the bedding can be used as the sensor 12 provided in the sleep state management device 1; the sensor is thus not limited to an accelerometer, and the sensors described in Patent Literature 2 and 3 may be used as well.

However, using an accelerometer makes it possible to detect movement in the bedding by carrying out the simple task of placing the sleep state management device 1 on the bedding, which makes it possible to reduce the burden placed on the measurement subject.

In the case where sensor that outputs only a single type of detection signal, such as a single-axis accelerometer, is used as the sensor 12, the process of step S3 in FIG. 3 can be omitted, and in step S4, the data conversion may be carried out by comparing the difference values calculated in step S2 with the threshold Th1.

Although step S10 is carried out before step S12 in FIG. 4, this order may be reversed.

In addition, although FIG. 4 illustrates an example in which both steps S10 and S11 and steps S12 and S13 are carried out, it is also possible to carry out only one of those two sets of steps.

Although the sleep state management device 1 employs a method in which the differences between adjacent peak values in the detection signals from the sensor 12 are calculated and whether or not there is body movement is determined based on these difference values, the method for determining whether or not there is body movement is not limited thereto, and a known method that employs the detection signals from the sensor 12 may be used instead.

A method such as that described in the present embodiment, in which the differences between adjacent peak values in the detection signals from the sensor 12 are calculated and whether or not there is body movement is determined based on these difference values, determines whether or not there is body movement in states where the detection signals contain noise components, and thus the processes of step S10 and on in FIG. 4 are particularly effective.

The respective steps illustrated in FIGS. 3 and 4 and executed by the control unit 14 of the sleep state management device 1 can also be executed by the electronic device 2 connected to the sleep state management device 1.

In this case, a program for causing a computer to execute the respective steps shown in FIGS. 3 and 4 and carried out by the control unit 14 of the sleep state management device 1 may be installed in the electronic device 2. Such a program is then recorded in a non-transitory recording medium from which the computer can read the program.

This computer-readable recording medium includes optical media such as a Compact Disc-ROM (CD-ROM), magnetic recording media such as memory cards, and so on. Further still, the program can be downloaded via a network and provided in such form.

Note that the embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

As described thus far, the following items are disclosed in the present specification.

A sleep state management device disclosed here manages a measurement subject's sleep state based on body movement in the measurement subject, and includes a sensor unit that detects movement in bedding where the measurement subject is sleeping and a body movement determination unit that determines whether or not there is body movement in the measurement subject using a detection signal from the sensor unit; in the case where at least one of a first period, in which a period without body movement in which it has been determined that there is no body movement using the detection signal or a period of body movement in which it has been determined that there is body movement using the detection signal occur cyclically, and a second period, in which the period of body movement continues for at least a predetermined amount of time, has occurred, the body movement determination unit corrects at least one of the period of body movement in the first period and the second period to a determination of a period without body movement.

A body movement determination unit in the sleep state management device disclosed here determines a period in which the period without body movement occurs cyclically as the first period.

The sleep state management device disclosed here further includes a peak value difference calculation unit that calculates a peak value difference that is a difference between adjacent peak values in the detection signal outputted from the sensor unit, and the body movement determination unit determines that a period in which a number of times the peak value difference exceeds a first threshold is greater than a predetermined value is a period in which the measurement subject's body has moved.

The sensor unit in the sleep state management device disclosed here is a two- or three-axis accelerometer.

The peak value difference in the sleep state management device disclosed here is an integrated value of the differences calculated for detection signals from each axis outputted from the sensor unit.

A sleep state management method disclosed here manages a measurement subject's sleep state based on body movement in the measurement subject, and includes a body movement determination step of determining body movement in the measurement subject using a detection signal from a sensor unit that detects movement in bedding where the measurement subject is sleeping; in the case where at least one of a first period, in which a period without body movement in which it has been determined that there is no body movement using the detection signal or a period of body movement in which it has been determined that there is body movement using the detection signal occur cyclically, and a second period, in which the period of body movement continues for at least a predetermined amount of time, has occurred, the body movement determination step corrects at least one of the period of body movement in the first period and the second period to a determination of a period without body movement.

A sleep state management program disclosed here is a program for causing a computer to execute the steps of the aforementioned sleep state management method.

INDUSTRIAL APPLICABILITY

The present invention can be applied in household sleep management devices, for example, and is useful in managing a user's health.

While the present invention has been described in detail with reference to a specific embodiment, it will be clear to one of ordinary skill in the art that many variations and modifications can be made without departing from the essential spirit and scope of the present invention. This application claims the benefit of Japanese Patent Application No. 2012-69609, filed Mar. 26, 2012, which is hereby incorporated by reference herein in its entirety.

REFERENCE SIGNS LIST 1 sleep state management device
11 display unit
12 sensor
13 operating unit
14 control unit

The invention claimed is:

1. A sleep state management device that manages a measurement subject's sleep state based on body movement in the measurement subject, the device comprising:
a sensor that is configured to detect movement in bedding where the measurement subject is sleeping;
a body movement determination unit that determines whether or not there is body movement in the measurement subject using a detection signal from the sensor;
a peak value difference calculation unit that calculates a peak value difference that is a difference between adjacent peak values in the detection signal outputted from the sensor,
wherein the body movement determination unit compares the peak value difference with a first threshold, and creates data by converting data at times where the peak value difference exceeds the first threshold to "1", and by converting data at times where the peak value difference is less than or equal to the first threshold to "0";
a recording medium that records the body movement using the created data in a time domain such that a first-type period in which the body movement exists and a second-type period in which the body movement does not exist are distinguishably recorded; and
a control unit that corrects the first-type period to the second-type period, in a case where the second-type period appears cyclically such that the first-type period and the second-type period appear alternately,
wherein the correction accomplished by the control unit is recorded on the recording medium.

2. The sleep state management device according to claim 1,
wherein the body movement determination unit determines that a period in which a number of times the peak value difference exceeds a first threshold is greater than a predetermined value is a period in which the measurement subject's body has moved.

3. The sleep state management device according to claim 2,
wherein the sensor is a two- or three-axis accelerometer.

4. The sleep state management device according to claim 3,
wherein the peak value difference is an integrated value of the differences calculated for detection signals from each axis outputted from the sensor.

5. A sleep state management method that manages a measurement subject's sleep state based on body movement in the measurement subject, the method comprising:
a body movement determination step of determining body movement in the measurement subject using a detection signal from a sensor that detects movement in bedding where the measurement subject is sleeping;
a peak value difference calculation step that calculates a peak value difference that is a difference between adjacent peak values in the detection signal outputted from the sensor,
wherein, during the body movement determination step, the peak value difference is compared with a first threshold, and data is created by converting data at times where the peak value difference exceeds the first threshold to "1", and by converting data at times where the peak value difference is less than or equal to the first threshold to "0";
a first recording step by a recording medium that records the body movement using the created data in a time domain such that a first-type period in which the body movement exists and a second-type period in which the body movement does not exist are distinguishably recorded;
a correcting step by a control unit that corrects the first-type period to the second-type period, in a case where the second-type period appears cyclically such that the first-type period and the second-type period appear alternately; and
a second recording step by the recording medium that records the correction accomplished by the control unit.

6. A non-transitory recording medium having a sleep state management program stored thereon that causes a computer to execute the steps of the sleep state management method according to claim 5.

7. A sleep state management device that manages a measurement subject's sleep state based on body movement in the measurement subject, the device comprising:
- a sensor that is configured to detect movement in bedding where the measurement subject is sleeping;
- a body movement determination unit that determines whether or not there is body movement in the measurement subject using a detection signal from the sensor;
- a peak value difference calculation unit that calculates a peak value difference that is a difference between adjacent peak values in the detection signal outputted from the sensor,
- wherein the body movement determination unit compares the peak value difference with a first threshold, and creates data by converting data at times where the peak value difference exceeds the first threshold to "1", and by converting data at times where the peak value difference is less than or equal to the first threshold to "0";
- a recording medium that records the body movement using the created data in a time domain such that a first-type period in which the body movement exists and a second-type period in which the body movement does not exist are distinguishably recorded; and
- a control unit that corrects the first-type period to the second-type period, in a case where the first-type period appears continuously for a time longer than a predetermined amount of time without any intervening of the second-type period,
- wherein the correction accomplished by the control unit is recorded on the recording medium.

* * * * *